(12) United States Patent
Pugliese et al.

(10) Patent No.: US 6,306,858 B1
(45) Date of Patent: Oct. 23, 2001

(54) ZWITTERIONIC FATTY ACID COMPOUNDS FOR ANTI-INFLAMMATION

(76) Inventors: Peter T. Pugliese, P.O. Box 307, Bernville, PA (US) 19506; Peter M. Pugliese, 51 Faust North Rd., Bethel, PA (US) 19507

(*) Notice: Subject to any disclaimer, the term of this patent is extended or adjusted under 35 U.S.C. 154(b) by 0 days.

(21) Appl. No.: 09/555,278
(22) PCT Filed: Nov. 25, 1998
(86) PCT No.: PCT/US98/25244
    § 371 Date: May 26, 2000
    § 102(e) Date: May 26, 2000
(87) PCT Pub. No.: WO99/27791
    PCT Pub. Date: Jun. 10, 1999

Related U.S. Application Data

(60) Provisional application No. 60/066,918, filed on Nov. 28, 1997.

(51) Int. Cl.$^7$ ..................................................... A61K 31/50
(52) U.S. Cl. ...................................... 514/252.12; 514/518
(58) Field of Search ............................... 514/252.12, 518

(56) References Cited

U.S. PATENT DOCUMENTS

| | | | |
|---|---|---|---|
| 4,544,656 | 10/1985 | O'Sullivan | 514/228 |
| 5,248,680 | 9/1993 | Bloomfield | 514/238.8 |
| 5,716,959 | 2/1998 | Theodore et al. | 514/255 |

*Primary Examiner*—Dwayne C. Jones
(74) *Attorney, Agent, or Firm*—Dinsmore & Shohl LLP

(57) ABSTRACT

Methods for treating muscular inflammation comprise applying to an inflamed area a therapeutically effective amount of a skin-compatible ester of a zwitterionic aminosulphonic acid of the formula

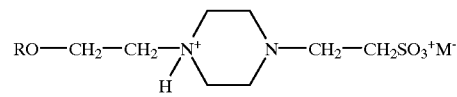

wherein M is an alkali metal and R is a straight chain aliphatic acid moiety. Compositions for treating inflammation comprising a therapeutically effective amount of a skin-compatible component comprising an ester, ether, urethane, amide or urea of at least one compound selected from a specified group. Additional methods for treating inflammation comprise applying to an inflamed area a therapeutically effective amount of a skin-compatible component comprising an ester, ether, urethane, amide or urea of at least one compound selected from a specified group.

15 Claims, No Drawings

ZWITTERIONIC FATTY ACID COMPOUNDS FOR ANTI-INFLAMMATION

CROSS REFERENCE TO RELATED APPLICATION

This application claims priority under 35 U.S.C. §119(e) of U.S. application Ser. No. 60/066,918, filed Nov. 28,1997.

FIELD OF THE INVENTION

This invention relates to pharmacologically-active, anti-inflammatory compounds, and more specifically to long aliphatic chain esters of selected zwitterionic organic compounds derived from naturally occurring taurine. This invention pertains to novel zwitterionic compounds with pharmacologic activity including, but not limited to, the use as an antiinflammatory.

BACKGROUND OF THE INVENTION

Any inflammation that occurs in the mammalian body is the clinical result of a sequence of events known as the arachidonic acid (ARA) cascade. Cell membranes consist of phospholipids. including fatty acids, one of which is ARA. In the inflammation process, the first step is the release of ARA from the phospholipid. The next step is the conversion of ARA into the specific mediator of inflammation. One pathway is the cyclooxygenase and the other is called the lipoxygenase pathway. Cortisone, along with other selected steroidal agents. block both inflammation pathways by inhibiting ARA release.

The mode of action of HEPES-ester is thought to be at the level of leukotrienes B4, but it is also possible that it occurs at higher levels in the inflammatory cascade, perhaps at the phospholipase A2 (PPLA2). Inhibition of PPLA2 action would arrest the aforedescribed cascade effect from being initiated.

Medical science looks for other biochemicals that lack the recognized side effects of prolonged steroid-based (cortisone) medications. One known human biochemical, taurine, synthesis of which occurs in the mammalian liver, and has demonstrated anti-inflammatory activity when administered centrally, but not when administered subcutaneously or interperitoneally. N-substituted derivatives of taurine include: 4-(2-Hydroxyethyl)-1-piperazine ethenesulfonic acid; $C_8H_{18}N_2O_4S$, which is commonly identified in the technical literature as HEPES (Merck Index, 12th edition monograph #4687). HEPES is available commercially from Angus Chemicals, as the sodium salt or, as the free acid. The scientific literature reports that intravenous injection of (14-C) HEPES, or of (3H) taurine, demonstrated rapid clearance, but with a significantly longer half-life compared with taurine. Mahon et al theorized that the greater anti-inflammatory effects of HEPES (sodium salt and the acid) compared with taurine, may be due to its slower systemic distribution or clearance, in vivo. The art suggest that HEPES is a significant agent to reduce cellular inflammation and cellular proliferation. However, the delivery systems for the HEPES treatment of inflammation remain to be optimized.

It is thus a principal object of this invention to provide a HEPES-based compound, an ester, and a pharmaceutical formulation including the ester, that is adapted for use in topically applied products to reduce symptoms of skin inflammation, wherein the particular etiology of the inflammation does not call for, or require, the use of antibiotics or germicidal compositions. The improved formulations for epidermal penetration, on bruises, muscle strains and sprains are also areas of useful treatment.

It is another object of the invention to combine the HEPES molecule with selected aliphatic acids, as the active ingredient of topical applications, which permit the HEPES moiety to penetrate the skin and so to better effect its anti-inflammatory nature.

It is a further object of the invention to provide a HEPES-containing active ingredient that is not limited to the known subcutaneous injection or IV infusion routes, but may also effective as a topical formulation.

A still further object of the invention is to provide HEPES esters as a cosmetic formulation ingredient, as a co-emulsifier, usable with topical analgesics.

Still another object of the invention is in a cosmetic preparation to incorporate an anti-skin ageing active ingredient.

These and other objects and benefits of this invention will become apparent from a study of the following specification.

SUMMARY OF THE INVENTION

The present invention relates to a composition and method for the treatment of inflammatory conditions in mammals, by the topical administration of selected Zwitterionic ester compositions, serving as safe and effective substances. Among useful Zwitterionic compounds which are preferred include PIPES, BES, POPSO, and preferably HEPES, when esterified, then alone, or in combination with other therapeutic ingredients (see PCT patent document). They are employed by applying to an affected area of the skin, a therapeutically effective amount of at least one skin compatible, Zwitterionic-Ester having the generic formula:

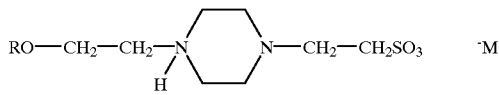

wherein M is an alkali metal and R is a naturally occurring, straight-chain, saturated or unsaturated, aliphatic acid, the esters of which form fatty acids in nature.

Preferably, Zwitterionic-ester has at least one pKa value at 20° C. in the range of 6.0–8.3 to permit its use on human skin, i.e., the ester exists mainly in its dipolar form, in the pH range of 6.0–8.3.

The isoelectric (ISO) point is the pH at which the net charge on a molecule in solution is 0. At this pH, amino acids exist almost entirely in the Zwitterionic state, i.e., the positive and negative groups are equally ionized. A solution of amino acids at the ISO point exhibits minimum conductivity, osmotic pressures, and viscosity.

Such dipolar molecules contain, for example, hydroxy groups and amino groups, and also acid groups, like phosphoric, carboxylic or sulfonics acid groups and, generally have pKa's in the range of 6.15–8.4.

Preferred aliphatic values for the ester moiety of HEPES ester are n-butanoic; isobutyric, n-valeric, palmitic, and stearic, behenyl, lauric, mynistic, (and their isomers) among the saturated aliphatics; and oleic and linoleic, among the unsaturated aliphatics.

The invention also provides a pharmaceutical composition for application to human skin in the treatment of inflammation comprising at least one of the above Zwitteronic-esters as the active ingredient, together with a pharmacologically acceptable topical carrier or base.

These esters may be used in the treatment of arthritis, myositis, insect bites, sunburn, psoriasis, atopic dermatitis, and other inflammatory processes of muscle, connective tissue, or skin appendages.

DETAILED DESCRIPTION OF THE INVENTION

The effective proportion of the active ingredient, by weight of the formulation, is in the range of 1 to 20%, preferably 5 to 10%. In the most preferred composition, the effective proportion lies in the range of 6 to 8. Not every compound falling within the general definition given above, is suitable for topical use in the method of the invention. Some few will prove to be contraindicated. Nevertheless, the exclusion of ineffective active ingredients is a matter well within the competence of the skilled pharmacologist in the conduct of the anti-inflammatory evaluation protocols for disclosed HEPES-esters.

The topical base is selected from a wide variety of compositions, formulated according to known principals for pharmaceutical purposes. Such compositions include creams, solids, ointments, lotions, and film-forming solutions among others. They may be presented in boxes, jars, or compressible tubes, both collapsible and non-collapsible. The solids may be presented as sticks for rubbing onto the skin. Some of the topical bases may be presented as papers, woven or non-woven fabric pieces, or pads, all being impregnated with composition.

The invention relates to HEPES derivatives which are pharmacologically active as anti-phospholipase and anti-inflammatory compounds specifically, wherein the active ingredients are certain long chain esters of selected zwitterionic compounds, based on an N-substituted taurine, namely aliphatic esters of HEPES.

The novel compounds may exist as at least one of the following five groups: ester, ether, urethane, amide, or urea of all of the following known compounds, and their salt forms. Preferred Zwitterionic-esters are prepared from the below listed sulfonic acids.

ACES—N-(2-Acetamido)-2 amino ethane sulfonic acid.
AMPSO—3-[1,1Dimethyl-2 hydroxyethyl amino]-2-hydroxypropane sulfonic acid.
BES—N,N-bis (Hydroxyethyl)-2 aminoethane sulfonic acid.
DIPSO—3-[N,N-bis (hydroxyl ethyl) amino]-2-hydroxypropane sulfonic acid.
CAPS—3-(cyclohexylamino)-1-propane sulfonic acid.
CAPSO—3-(cyclohexylamino)-1-propane sulfonic acid.
CHES—2-(N-cyclohexylamino) ethane sulfonic acid.
HEPPS—N-(2-hydroxy ethyl) piperazine-N'-3-propane sulfonic acid.
HEPES—N-(2-hydroxy ethyl) piperazine, N'-(2-ethane sulfonic acid).
HEPPSO—N-(2-hydroxy ethyl) piperazine-N'-2-hydroxypropane sulfonic acid.
MES—2-(N-Morpholino) ethane sulfonic acid.
MOPS—3-(N-Morpholino) propane sulfonic acid.
MOPSO—3-(N-Morpholino)-2 hydroxy propane sulfonic acid.
PIPES—Piperazine-N, N'-bis (2 ethane sulfonic acid).
New Mono PIPES—Piperazine-N'-(2 ethane sulfonic acid).
POPSO—Piperazine-N, N'-bis (2-hydroxy propane sulfonic acid).
TAPS—3-[N-tris-(hydroxy methyl) methyl amine]-2-hydroxy propane sulfonic acid.
TES—N-tris-(hydroxy methyl)-methyl-2-amine ethane sulfonic acid.

The precursor compounds listed above are best known in the literature as biological buffers. Many are commonly used as buffering agents in mammalian cell cultures. Manufacturers of these compounds include Angus Chemicals, SIGMA, and British Drug House.

Synthesis of HEPES Esters

Generally, an alkali metal salt of HEPES is catalytically reacted with an alkyl-substituted, either saturated or unsaturated aliphatic salt, such as methyl oleate, methyl linoleate, methyl palmitate, methyl stearate, methyl myristate, and methyl behenate. They are reacted in equi-molecular amounts carried out either with or without a non-aqueous solvent, such as acetone, and in a temperature range of 0° C. to (variable)° C. which is between 0° C. and the solvent's reflux temperature. The purification of the crude ester is carried out by means of crystallization in an organic solvent, dissolved in methanol, and recrystallized. As to analytical methodology, preparative high pressure liquid chromatography (HPLC) is followed by TLC, HPLC, and nuclear magnetic resonance (NMR). Potentiometric titration and bromic titration are done across the double bond to establish identity and purity. The HPLC device is equipped with a variable length, ultraviolet detector.

Protocol to Evaluate Candidate Formulations for Suppression of Induced Skin Inflammations Sodium lauryl sulfate solution 0.5% is applied in a patch to four areas on the volar surface forearm. Site one is pretreated with a base formula, site two is pretreated with the base formula plus 10% HEPES ester, while sites three and four are left untreated.

After 24 hours, the sites are examined, the erythema and edema on sites one and two are recorded by photographs. Site one is treated with the base product, site three is treated with the base product plus 10% HEPES ester, and site two and four are untreated controls. Each treated site is treated four times a day. The observed results are recorded as the percent reduction of erythema and edema at the HEPES ester-treated sites over the base formula and two control treated sites.

Working Example 1

Active ingredients synthesis procedure (that effect the HEPES-oleate synthesis)

Preparation of HEPES ($C_8H_{18}N_2O_4S$)-Oleate Ester

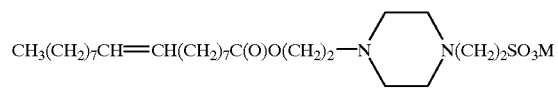

The preparation of Compound I is characterized by catalytically reacting 4-(2-Hydroxyethyl) piperazine-1-ethanesulfonic acid, with salts, like methyl oleate, substituted, $C_{17}H_{33}CO_2CH_3$, in equimolar amounts. The reaction can be carried out in a non-aqueaous solvent. Sodium methoxide is a useful catalyst. The reaction temperature may vary between 0° C. and the solvent reflux temperature. The purification of the compound is carried out by means of crystallization in a solvent such as acetone.

I. The Esters.

Methyl oleate HEPES Na+Na methoxide→HEPES oleate+Methyl alcohol HEPES Na oleate

HEPES Esters Generic Formula

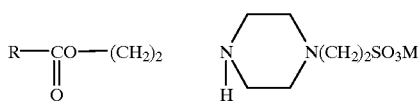

The preparation of compound I can be carried out by reacting a fatty acid with HEPES or any one of its salt derivatives. One preferred process route is to react HEPES, sodium salt, with methyl oleate and sodium methoxide as a catalyst.

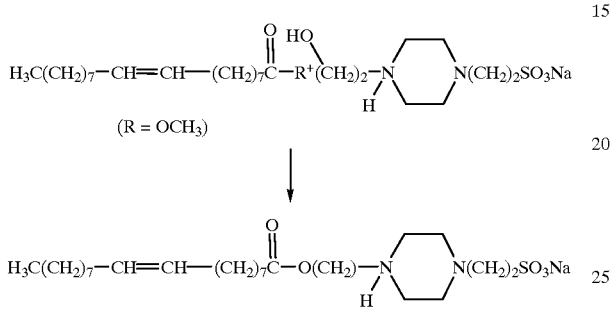

The reaction is carried out with an excess of methyl oleate as a solvent. To ensure the completion of the reaction, removal of side product methanol is carried out.

Preparation of the HEPES oleate sodium salt: 4-(2-Hydroxyethyl) piperazine-1-ethanesulfonic acid, sodium salt, is slowly added to a stirring flask of methyl oleate in equal molar equivalents. The mixture is stirred at room temperature for 15 minutes. Then a catalytic quantity of sodium methoxide is slowly added to the stirring mixture. The reaction mix is stirred for less than five minutes. The reaction mix is then slurried in acetone, then isolated and dried, affording greater than an 80% yield of the title oleate as a white to off-white solid, to wit:

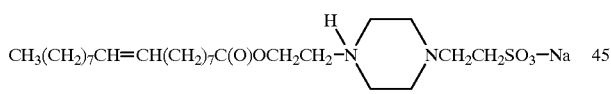

EXAMPLE 1

In a 500 ml 3 neck flask, 114 gms of methyl oleate is added with 100 gms of HEPES, sodium salt (source: Angus Chemical); while stirring, the mixture is warmed to 27–30° C. Once and the contents are slowly heated to 45–50° C. Once at 45–50° C., vacuum is applied to remove methanol to ensure reaction completion.

After two hours at 45–50° C. and under vacuum, the reaction is complete. The vacuum is removed and acetone is added. With the reaction mix in acetone solution, it is slowly cooled to 0–5° C. over two hours, and stirred for an additional six hours before isolating the HEPES oleate, sodium salt, in a filter funnel. The white to off-white solid product is then placed in a vacuum oven at 50° C. at 28" of vacuum for six hours to remove any remaining acetone or methanol. A greater than 80% yield is obtained.

Working Example 2

II. HEPES ether has the structure:

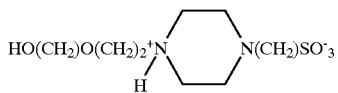

HEPES, Na salt, is reacted with ethylene oxide to form the ether of the below generic structural formula:

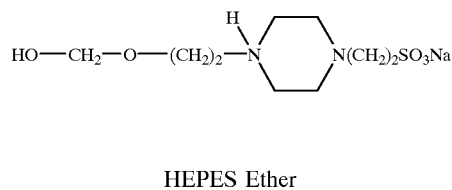

HEPES Ether

Working Example 3

III. HEPES urethane has the structure:

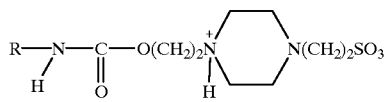

The reaction is carried out by adding isocyanate to the HEPES to form the corresponding urethane below:

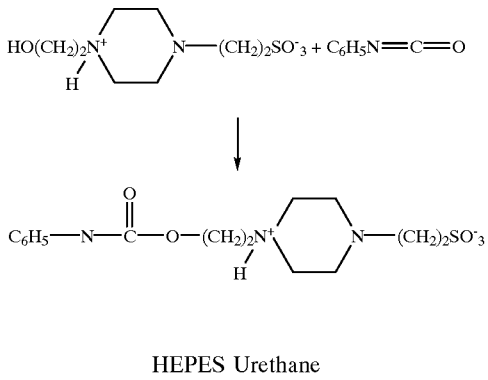

HEPES Urethane

Working Example 4

Certain other analogs and derivatives of HEPES can be synthesized, such as Piperazine-N'-(2-ethane sulfonic acid) I. This can be seen as the mono N-substituted analog. Another prospective analog is the N-Methylpiperazine-N'-(2 ethane sulfonic acid), II, that is readily prepared. Also, the piperidine analog, III, of the piperazine ester (Comp I) may be usefully synthesized and evaluated,

I

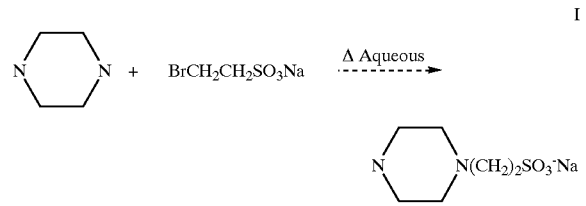

-continued

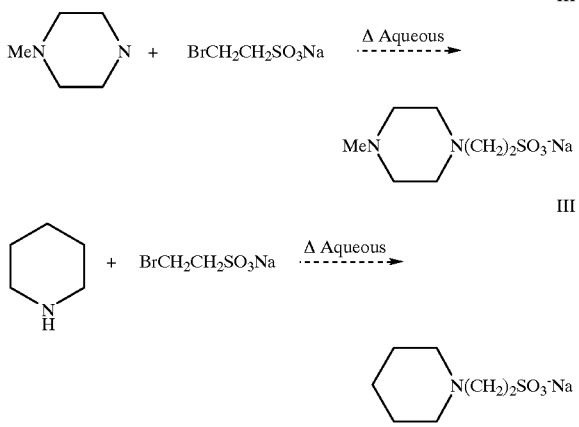

What is claimed is:

1. A method for treating muscular inflammation, comprising applying to an inflamed area a therapeutically effective amount of a skin-compatible ester of a zwitterionic aminosulphonic acid of the formula

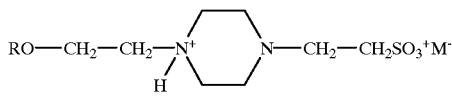

wherein M is an alkali metal and R is a straight chain aliphatic acid moiety.

2. A method according to claim 1, wherein R is selected from the group consisting of n-butanoic, isobutyric, n-valeric, palmitic, stearic, behenyl, lauric, myristic, oleic and linoleic acid moieties.

3. A method according to claim 1, wherein the ester has at least one pKa value at 20° C. in the range of 6.0–8.3.

4. A method according to claim 1, wherein the ester is applied in a pharmacologically acceptable topical carrier.

5. A method according to claim 4, wherein the pharmacologically acceptable topical carrier is in solid or lotion form.

6. A method according to claim 1, wherein the ester is the oleic acid ester of N-(2-hydroxyethyl)piperazine-N'-(2-ethane sulfonic acid) (HEPES).

7. A method according to claim 1, wherein the ester is the linoleic acid ester of N-(2-hydroxyethyl)piperazine-N'-(2-ethane sulfonic acid) (HEPES).

8. A method for treating inflammation, comprising applying to an inflamed area a therapeutically effective amount of a skin-compatible component comprising an ester, ether, urethane, amide or urea of at least one compound selected from the group consisting of N-(2-acetamido)-2-aminoethane sulfonic acid (ACES),
3-[1,1-dimethyl-2-hydroxyethyl amino]-2-hydroxypropane sulfonic acid (AMPSO),
N,N-bis (hydroxyethyl)-2-aminoethane sulfonic acid (BES),
3-[N,N-bis (hydroxyethyl) amino]-2-hydroxypropane sulfonic acid (DIPSO),
3-(cyclohexylamino)-1-propane sulfonic acid (CAPS),
3-(cyclohexylamino)-1-hydroxypropane sulfonic acid (CAPSO),
2-(N-cyclohexylamino) ethane sulfonic acid (CHES),
N-(2-hydroxyethyl) piperazine-N'-3-propane sulfonic acid (HEPPS),
N-(2-hydroxyethyl) piperazine-N'-2-hydroxypropane sulfonic acid (HEPPSO),
2-(N-morpholino) ethane sulfonic acid (MES),
3-(N-morpholino) propane sulfonic acid (MOPS),
3-(N-morpholino)-2-hydroxypropane sulfonic acid (MOPSO),
piperazine-N,N'-bis (2-ethane sulfonic acid) (PIPES),
piperazine-N'-(2-ethane sulfonic acid) (mono PIPES),
piperazine-N,N'-bis (2-hydroxypropane sulfonic acid) (POPES),
3-[N-tris-(hydroxymethyl) methyl amine]-2-hydroxypropane sulfonic acid (TAPS), and
N-tris-(hydroxymethyl) methyl-2-amine ethane sulfonic acid (TES).

9. A method according to claim 8, wherein the skin-compatible component has at least one pKa value at 20° C. in the range of 6.0–8.3.

10. A method according to claim 8, wherein the inflammation is associated with arthritis, myositis, insect bites, sunburn, psoriasis, or atopic dermatitis.

11. A method according to claim 8, wherein the method is for treating muscle inflammation.

12. A method according to claim 8, wherein the method is for treating skin inflammation.

13. A method according to claim 8, wherein the ester, ether, urethane, amide or urea is applied in a pharmacologically acceptable topical carrier.

14. A method according to claim 13, wherein the pharmacologically acceptable topical carrier is in solid or lotion form.

15. A composition for treating inflammation, comprising a therapeutically effective amount of a skin-compatible component comprising an ester, ether, urethane, amide or urea of at least one compound selected from the group consisting of N-(2-acetamido)-2-aminoethane sulfonic acid (ACES),
3-[1,1-dimethyl-2-hydroxyethyl amino]-2-hydroxypropane sulfonic acid (AMPSO),
N,N-bis (hydroxyethyl)-2-aminoethane sulfonic acid (BES),
3-[N,N-bis (hydroxyethyl) amino]-2-hydroxypropane sulfonic acid (DIPSO),
3-(cyclohexylamino)-1-propane sulfonic acid (CAPS),
3-(cyclohexylamino)-1-hydroxypropane sulfonic acid (CAPSO),
2-(N-cyclohexylamino) ethane sulfonic acid (CHES),
N-(2-hydroxyethyl) piperazine-N'-3-propane sulfonic acid (HEPPS),
N-(2-hydroxyethyl) piperazine-N'-2-hydroxypropane sulfonic acid (HEPPSO),
2-(N-morpholino) ethane sulfonic acid (MES),
3-(N-morpholino) propane sulfonic acid (MOPS),
3-(N-morpholino)-2-hydroxypropane sulfonic acid (MOPSO),
piperazine-N,N'-bis (2-ethane sulfonic acid) (PIPES),
piperazine-N'-(2-ethane sulfonic acid) (mono PIPES),
piperazine-N,N'-bis (2-hydroxypropane sulfonic acid) (POPES),
3-[N-tris-(hydroxymethyl) methyl amine]-2-hydroxypropane sulfonic acid (TAPS), and
N-tris-(hydroxymethyl) methyl-2-amine ethane sulfonic acid (TES).

* * * * *